(12) United States Patent
Wahl

(10) Patent No.: US 12,251,103 B2
(45) Date of Patent: Mar. 18, 2025

(54) SURGICAL BENDING INSTRUMENT

(71) Applicant: In2Bones USA, LLC, Memphis, TN (US)

(72) Inventor: Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 161 days.

(21) Appl. No.: 17/853,840

(22) Filed: Jun. 29, 2022

(65) Prior Publication Data
US 2022/0323069 A1    Oct. 13, 2022

Related U.S. Application Data

(60) Continuation of application No. 16/827,827, filed on Mar. 24, 2020, now Pat. No. 11,382,619, which is a continuation of application No. 16/028,189, filed on Jul. 5, 2018, now Pat. No. 10,610,221, which is a division of application No. 15/041,959, filed on Feb. 11, 2016, now Pat. No. 10,052,103.

(60) Provisional application No. 62/116,387, filed on Feb. 14, 2015.

(51) Int. Cl.
| | |
|---|---|
| A61B 17/068 | (2006.01) |
| A61B 17/064 | (2006.01) |
| A61B 17/072 | (2006.01) |
| A61B 17/88 | (2006.01) |

(52) U.S. Cl.
CPC ........ *A61B 17/068* (2013.01); *A61B 17/0642* (2013.01); *A61B 17/0682* (2013.01); *A61B 17/072* (2013.01); *A61B 17/8863* (2013.01); *A61B 2017/0645* (2013.01); *A61B 2017/07235* (2013.01)

(58) Field of Classification Search
CPC .................................................. A61B 17/068
See application file for complete search history.

(56) References Cited

U.S. PATENT DOCUMENTS

| | | | | |
|---|---|---|---|---|
| 3,559,952 A | * | 2/1971 | Skinner ................. | F16K 31/445 251/347 |
| 3,960,147 A | * | 6/1976 | Murray .............. | A61B 17/8872 606/101 |
| 2009/0101692 A1 | * | 4/2009 | Whitman ............... | A61B 90/98 227/175.1 |

(Continued)

*Primary Examiner* — Christian A Sevilla
(74) *Attorney, Agent, or Firm* — Rutan & Tucker LLP; Hani Z. Sayed

(57) ABSTRACT

An apparatus and a method are provided for a surgical bending instrument for bending surgical implants. The surgical bending instrument comprises a body including a longitudinally extending threaded hole. A shaft comprising a threaded portion is rotatably engaged within the threaded hole. A handle is coupled to a proximal end of the shaft, and a distal extension of the shaft comprises a driver. A distal force applicator comprises the driver centered between a first grip and a second grip. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone.

18 Claims, 4 Drawing Sheets

(56) References Cited

U.S. PATENT DOCUMENTS

| | | | |
|---|---|---|---|
| 2013/0098966 A1* | 4/2013 | Kostrzewski | A61B 17/07207 606/1 |
| 2015/0133940 A1* | 5/2015 | Palmer | A61B 17/068 606/75 |

* cited by examiner

SURGICAL BENDING INSTRUMENT

PRIORITY

This application claims the benefit of and priority to U.S. patent application Ser. No. 16/827,827, filed Mar. 24, 2020 which is a continuation of U.S. patent application Ser. No. 16/028,189, filed Jul. 5, 2018, now U.S. Pat. No. 10,610,221, which is a divisional of U.S. patent application Ser. No. 15/041,959, filed Feb. 11, 2016, which claims the benefit of priority to U.S. Provisional Application No. 62/116,387, filed Feb. 14, 2015, all of which are incorporated herein in their entireties.

FIELD

The field of the present disclosure generally relates to securing bones together. More particularly, the field of the disclosure relates to an apparatus and a method for a surgical bending instrument for implanting surgical implants at bone fixation or fusion sites of a patient.

BACKGROUND

Surgical staples or a fusion bone plate implant utilized in conjunction with one or more fasteners may be used to generate compression and stability at a bone interface. An implant generally serves to stabilize bones, or bone parts, relative to one another so as to promote bone fusion. In many applications, surgical staples, or bone plates and fasteners are used to fuse bones, or bone parts, of the human body, such as bones in the foot, the ankle, the hand, the wrist, as well as various other portions of the body. Surgical staples are particularly advantageous in the hands and feet due to a low dorsal profile of the staples once they are implanted. Furthermore, during the course of certain medical procedures, a surgeon may immobilize one or more bones or bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus and a method are provided for a surgical bending instrument for bending surgical implants. The surgical bending instrument comprises a body including a longitudinally extending threaded hole. A shaft comprising a threaded portion is rotatably engaged within the threaded hole. A handle is coupled to a proximal end of the shaft, and a distal extension of the shaft comprises a driver. A distal force applicator comprises the driver centered between a first grip and a second grip. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone. The surgical bending instrument may be packaged into sterile surgery-specific kits comprising other surgical tools, such as drill guides, drill sizers, tamps, forceps, staple removal tools, drills, temporary pins, drill depth stops, fusion bone plates, bone plate fasteners, compression screws, and the like.

In an exemplary embodiment, a surgical bending instrument for bending surgical implants comprises a body supporting a distal force applicator and a proximal handle; a first grip and a second grip of the distal forced applicator configured to retain the surgical implant; and a driver of the distal force applicator configured to exert a distally-directed force so as to bend the surgical implant.

In another exemplary embodiment, a shaft is threadably engaged within a longitudinally extending hole within the body, a distal extension of the shaft comprising the driver, and a proximal handle is fixedly coupled to a proximal end of the shaft. In another exemplary embodiment, the driver and the shaft are separate components that are engaged with one another. In another exemplary embodiment, the shaft communicates mechanical forces applied at the proximal handle to the driver. In another exemplary embodiment, rotating the proximal handle relative to the body moves the driver longitudinally relative to the body. In another exemplary embodiment, twisting the proximal handle clockwise moves the driver distally into contact with the crown, such that the surgical staple is clasped between the grips and the driver, wherein further clockwise twisting of the proximal handle changes the surgical staple from an initial configuration to a distracted configuration suitable for implantation across a bone fusion or fixation site of a patient. In another exemplary embodiment, twisting the proximal handle counterclockwise retracts the driver proximally away from the crown, allowing the surgical staple to relax from the distracted configuration and compress the bone fusion or fixation site.

In another exemplary embodiment, a lever comprising a wheel and a peripheral cam is rotatably mounted on a pivot within the body, such that when the lever is moved proximally, the cam forceably pushes the driver so as to exert a distally-directed force onto the surgical implant. In another exemplary embodiment, a lever comprising a wheel and a peripheral cam is rotatably mounted on a pivot within the body, such that moving the lever proximally causes the cam to exert a distally-directed force onto the surgical implant. In another exemplary embodiment, the surgical bending instrument comprises a rigid material suitable for bending surgical implants.

In another exemplary embodiment, the distal force applicator is configured to retain a surgical staple, such that the surgical staple may be changed to a distracted configuration suitable for implantation at a bone fixation or fusion site of a patient. In another exemplary embodiment, the surgical staple is indicated for fixation of osteotomies and joint arthrodesis of the hands and feet. In another exemplary embodiment, the distal force applicator is configured to bend a bone fusion plate so as to tailor the plate to specific anatomy of a patient's bone.

In another exemplary embodiment, the first and second grips are configured to support a crown of a surgical staple when the driver is placed into forceable contact with the center of the crown. In another exemplary embodiment, the driver and the grips operate to retain the surgical staple within the distal force applicator, thereby facilitating implanting the staple into the patient. In another exemplary embodiment, the first and second grips engage the surgical staple on opposite sides of the crown, thereby preventing the surgical staple from becoming dislodged from the distal force applicator during implantation into a patient. In another exemplary embodiment, the first and second grips have a separation distance comparable with the length of the crown. In another exemplary embodiment, the first and second grips have an adjustable separation distance so as to facilitate using the surgical bending instrument with a variety of differently-sized staples.

In another exemplary embodiment, the surgical bending instrument is packaged into sterile surgery-specific kits comprising other surgical tools, such as drill guides, drill sizers, tamps, forceps, staple removal tools, drills, temporary pins, drill depth stops, fusion bone plates, bone plate fasteners, compression screws, and the like.

In an exemplary embodiment, a method of using a surgical bending instrument for implanting a surgical staple at a bone fixation or fusion site of a patient comprises loading the surgical staple into a distal force applicator of the surgical bending instrument, such that the surgical staple is in contact with a first grip and a second grip; advancing a driver into forceable contact with a crown of the surgical staple, the surgical staple being clasped between the first grip, the second grip, and the driver; distracting the surgical staple, such that a first leg and a second leg of the surgical staple are parallel to one another; inserting the surgical staple through an incision and sliding the first and second legs into parallel holes drilled across a bone fusion or fixation site of the patient; retracting the driver from the crown so as to allow the surgical staple to compress the bone fusion or fixation site; disengaging the first and second grips from the crown; pushing the surgical staple into the parallel holes until the crown is in contact with the patient's bone; and closing the incision by way of suturing.

In another exemplary embodiment, advancing further comprises rotating a proximal handle clockwise so as to move the driver distally into contact with the crown, the driver being connected to the proximal handle by way of a threaded shaft extending longitudinally through the surgical bending instrument. In another exemplary embodiment, distracting the surgical staple further comprises twisting the proximal handle clockwise to move the driver distally into the crown until the first and second legs are parallel with one another. In another exemplary embodiment, retracting further comprises rotating the proximal handle counterclockwise so as to move the driver proximally away from the crown, thereby allowing the first and second legs to bend toward one another.

BRIEF DESCRIPTION OF THE DRAWINGS

The drawings refer to embodiments of the present disclosure in which.

Figure 1:
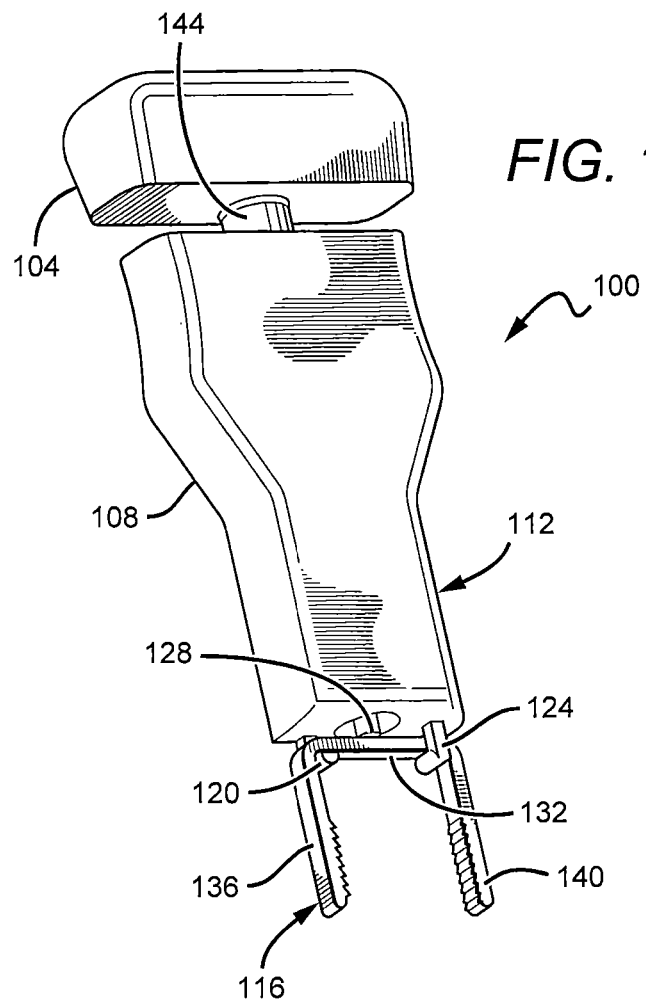
FIG. 1 illustrates an upper perspective view of an exemplary embodiment of a surgical bending instrument in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first implant," may be made. However, the specific numeric reference should not be interpreted as a literal sequential order but rather interpreted that the "first implant" is different than a "second implant." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for a surgical bending instrument for bending surgical implants. The surgical bending instrument comprises a body including a longitudinally extending hole, at least of portion of which comprising threads. A shaft comprising a threaded portion passes through hole and is rotatably engaged with the threads in the hole. A handle is fixedly coupled to a proximal end of the shaft, and a distal extension of the shaft comprises a driver. A distal force applicator comprises a first grip, a second grip, and the driver centered between the first and second grips. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone.

FIG. 1 illustrates a perspective view of an exemplary embodiment of a surgical bending instrument 100 in accordance with the present disclosure. The surgical bending instrument 100 comprises a proximal handle 104, a body 108, and a distal force applicator 112. In the embodiment illustrated in FIGS. 1-2, a surgical staple 116 is shown loaded within the distal force applicator 112, such that the surgical staple 116 is in a distracted configuration suitable for implantation at a bone fixation or fusion site of a patient. The surgical staple 116 generally is of the variety indicated for fixation of osteotomies and joint arthrodesis of the hands and feet. As such, the surgical staple 116 preferably is comprised of a metal alloy exhibiting shape memory and superelastic properties, such as Nitinol or other similar material. It should be understood, however, that the surgical bending instrument 100 is not to be limited to distracting surgical staples, but rather may be used in various other capacities, such as by way of non-limiting example, bending a bone fusion plate so as to tailor the plate to specific anatomy of a patient's bone being treated.

Figure 2:
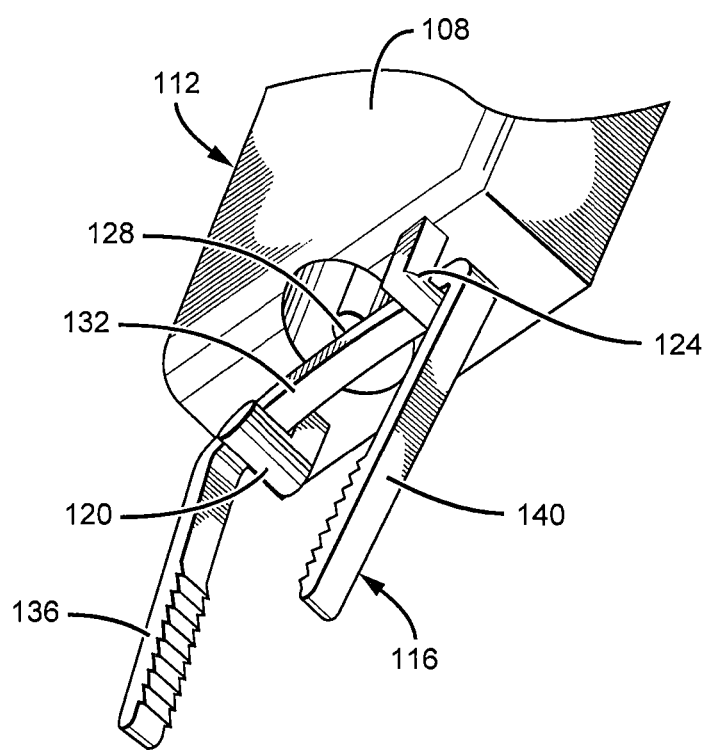
FIG. 2 illustrates a lower perspective view of an exemplary embodiment of a distal force applicator, according to the present disclosure.

As best illustrated in FIG. 2, the distal force applicator 112 comprises a first grip 120, a second grip 124, and a driver 128 centered there between. The first and second grips 120, 124 are configured to cooperate so as to support a crown 132 of the surgical staple 116 when the driver 128 is placed into forceable contact with the center of the crown 132. The forces on the crown 132 due to the driver 128 and the grips 120, 124 operate to retain the surgical staple 116 within the distal force applicator 112, thereby facilitating implanting the staple into the patient. As shown in FIG. 2, the first and second grips 120, 124 are configured to engage the surgical staple 116 on opposite sides of the crown 132. As will be appreciated, engaging the crown 132 on opposite sides advantageously prevents the staple from becoming dislodged from the distal forced applicator 112 during distracting the staple or implantation into the patient.

Figure 3A:
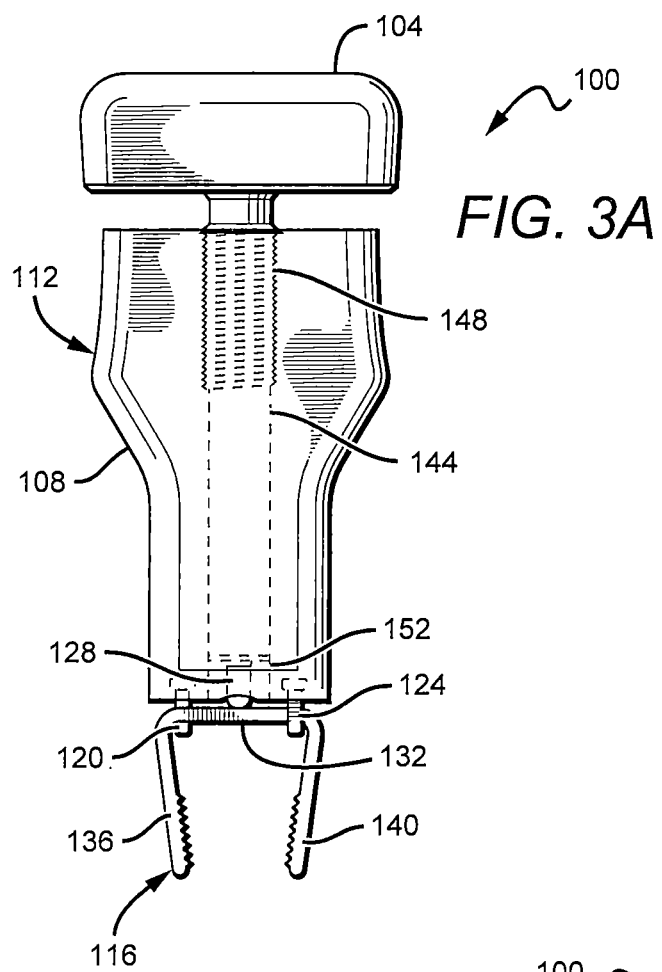
FIG. 3A illustrates a ghost view of an exemplary embodiment of a surgical bending instrument retaining a surgical staple in an initial configuration, according to the present disclosure.
Figure 3B:
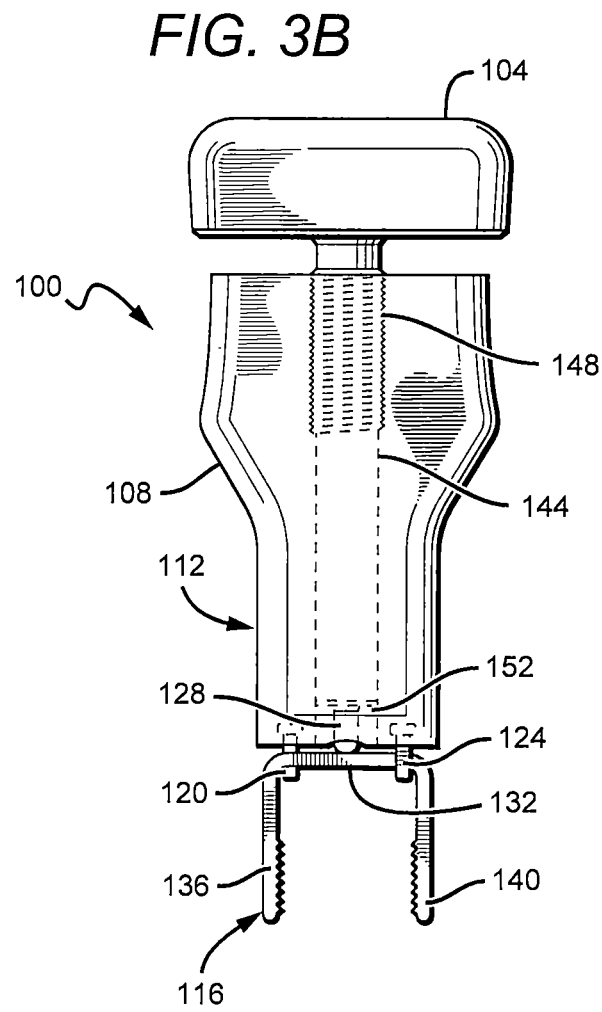
FIG. 3B illustrates a ghost view of the exemplary embodiment of the surgical bending instrument illustrated in FIG. 3A distracting the surgical staple in accordance with the present disclosure.

Preferably, the first and second grips 120, 124 have a separation distance comparable with the length of the crown 132. Thus, as illustrated in FIGS. 3A-3B, the first grip 120 is positioned near a first leg 136 of the surgical staple 132, and the second grip 124 is positioned near a second leg 140 of the staple. It will be appreciated, therefore, that the distal force applicator 112 of the surgical bending instrument 100 is configured to be used with specific sizes of surgical staples 116. In some embodiments, the surgical bending instrument 100 may be configured with an overall size so as to be used with specific sizes of surgical staples 116. In some embodiments, a color-matching system may be utilized to indicate to the surgeon that certain surgical staples 116 may be implanted by way of the surgical bending instrument 100. Further, in some embodiments, the first and second grips 120, 124 may have an adjustable separation distance so as to facilitate using the surgical bending instrument 100 with a variety of differently-sized staples.

FIGS. 3A and 3B illustrate ghost views of the exemplary embodiment of the surgical bending instrument 100 illustrated in FIGS. 1-2. A shaft 144 passing through the body 108 comprises a threaded portion 148 and the above-mentioned driver 128. In the illustrated embodiment, the driver 128 comprises a distal extension of the shaft 144, having a narrower diameter than proximal portions of the shaft 144. In some embodiments, however, the driver 128 and the shaft 144 are separate components which are engaged with one another. It will be appreciated that the shaft 144 communicates mechanical forces applied at the proximal handle 104 to the driver 128, and thus to the crown 132 of the staple. In the illustrated embodiment, the threaded portion 148 is rotatably engaged with similar threads within a hole 152 extending longitudinally through the body 108. The shaft 144 is fixedly coupled with the proximal handle 104 such that rotating the proximal handle 104 relative to the body 108 rotates the shaft 144 within the hole 152, and thus moves the driver 128 longitudinally relative to the body 108.

As best illustrated in FIG. 3A, when the driver 128 is not in contact with the crown, the surgical staple 116 is in an initial configuration wherein the first leg 136 and the second leg 140 of the staple bend toward one another. During operation of the surgical bending instrument 100, twisting the proximal handle 104 clockwise, as viewed from the perspective of a surgeon operating the instrument 100, advances the shaft 144 and moves the driver 128 distally toward the crown 132. Once the driver 128 contacts the center of the crown 132, the surgical staple 116 becomes clasped between the grips 120, 124 and the driver 128. Further clockwise twisting of the proximal handle 104 exerts an increasing degree of force onto the crown 132 by the grips 120, 124 and the driver 128. As will be appreciated, the distally-directed force due to the driver 128 and proximally-directed forces due to the grips 120, 124 cause a corresponding distraction of the first and second legs 136, 140. Thus, clockwise twisting of the proximal handle 104 enables the surgeon to change the surgical staple 116 from the initial configuration, shown in FIG. 3A, to a distracted configuration wherein the first and second legs 136, 140 are forced into a parallel relationship, as illustrated in FIG. 3B.

Once the surgical staple 116 is in the distracted configuration, the surgeon may use the surgical bending instrument 100 to slide the first and second legs 136, 140 into parallel holes drilled across a bone fusion or fixation site of a patient. It will be appreciated that the threaded portion 148 keeps the driver 128 in contact with the crown 132, thereby maintaining the distracted configuration of the surgical staple 116 during implantation. The surgeon may insert the first and second legs 136, 140 into the parallel holes until the first and second grips 120, 124 come into contact with the patient's bone. The surgeon may then twist the proximal handle 104 counterclockwise so as to retract the driver 128 proximally away from the crown 132, thereby allowing the surgical staple 116 to relax from the distracted configuration. The shape memory and superelastic properties of the material comprising the surgical staple 116 ensure that the staple advantageously compresses the bones to be fused as the staple attempts to return to the initial configuration illustrated in FIG. 3A. Once the driver 128 has been suitably retracted from the crown 132, the surgeon may disengage the first and second grips 120, 124 from the crown and then use a tamp to push the legs 136, 140 into the parallel holes until the crown 132 is in direct contact with the bone. The surgeon may then close the incision by way of suturing.

As will be recognized, some surgical procedures may necessitate removing a surgical staple, such as the surgical staple 116, from a bone fusion or fixation site of a patient. It is envisioned that the surgeon may lift the crown 132 away from the patient's bone surface by way of a suitable removal tool so as to create enough clearance for the surgeon to engage the grips 120, 124 between the bone and the crown 132. With the first and second grips 120, 124 suitably engaged with the crown 132, the surgeon may turn the proximal handle 104 clockwise to distally advance the driver 128 into contact with the center of the crown 132. Upon twisting the proximal handle 104 so as to place the surgical staple 116 into the distracted configuration illustrated in FIG. 3A, the surgeon may use the surgical bending instrument 100 to pull the first and second legs 136, 140 free of the patient's bone.

Figure 4A:
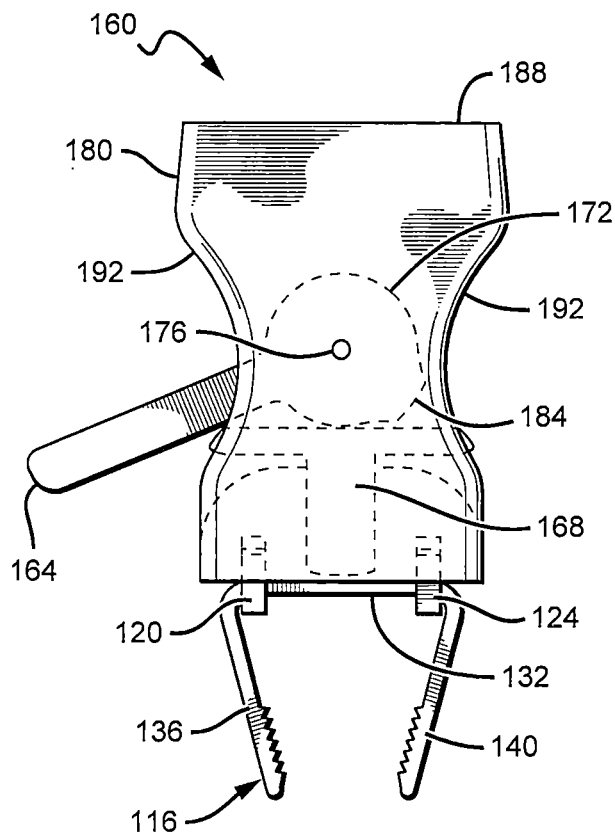
FIG. 4A illustrates a ghost view of an exemplary embodiment of a surgical bending instrument retaining a surgical staple in an initial configuration, according to the present disclosure.
Figure 4B:
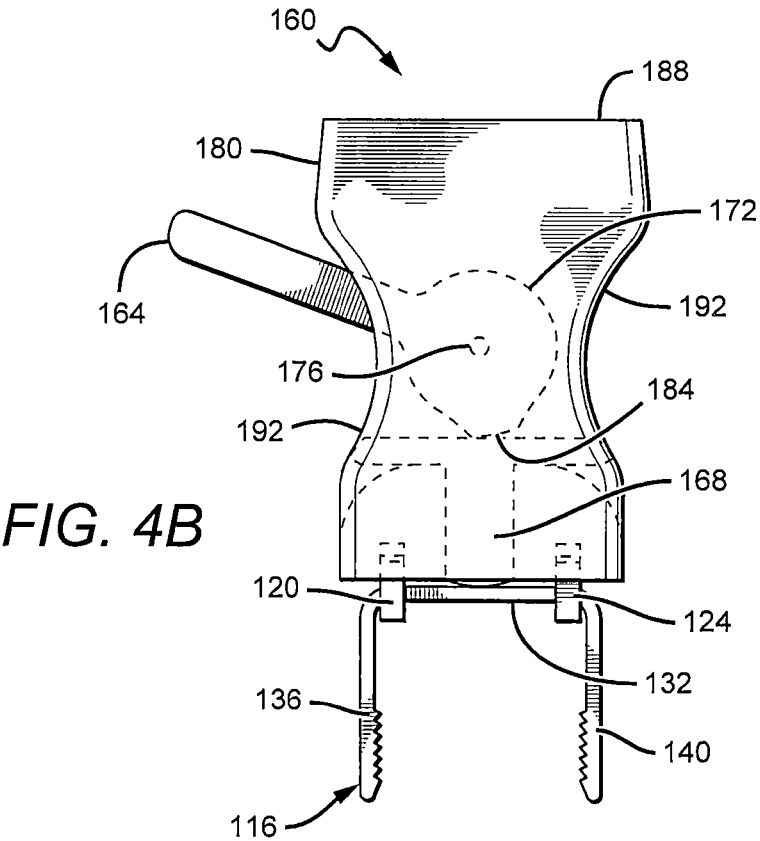
FIG. 4B illustrates a ghost view of the exemplary embodiment of the surgical bending instrument illustrated in FIG. 4A distracting the surgical staple in accordance with the present disclosure.

FIGS. 4A and 4B illustrate ghost views of an exemplary embodiment of a surgical bending instrument 160 retaining the surgical staple 116 in accordance with the present disclosure. The surgical bending instrument 160 illustrated in FIGS. 4A-4B is similar to the surgical bending instrument 100 illustrated in FIGS. 1-2, with the exception that the surgical bending instrument 160 comprises a side lever 164 coupled with a driver 168. The side lever 164 comprises a wheel 172 which is rotatably mounted on a pivot 176 within a body 180 of the surgical bending instrument 160. The wheel 172 is in sliding contact with a proximal portion of the driver 168, such that the side lever 164 may be rotated from a distal position, illustrated in FIG. 4A, to a proximal position as shown in FIG. 4B. The wheel 172 further comprises a cam 184 configured to push the driver 168 distally within the body 180 into the crown 132 when the side lever 164 is rotated to the proximal position. As will be appreciated, the cam 184 and the driver 168 exert a distally-directed force onto the crown 132, thereby distracting the surgical staple 116, as illustrated in FIG. 4B and described herein with respect to FIGS. 3A and 3B.

It will be appreciated that moving the side lever 164 to distract the surgical staple 116 requires a degree of force to be placed onto the lever. A proximal surface 188 of the body 180 advantageously facilitates grasping and stabilizing the surgical bending instrument 160 while the side lever 164 is moved during distraction of the surgical staple 116. A narrow midsection 192 of the body 180 further enables grasping and stabilizing the surgical bending instrument 160 during distraction of the staple 116.

Figure 5A:
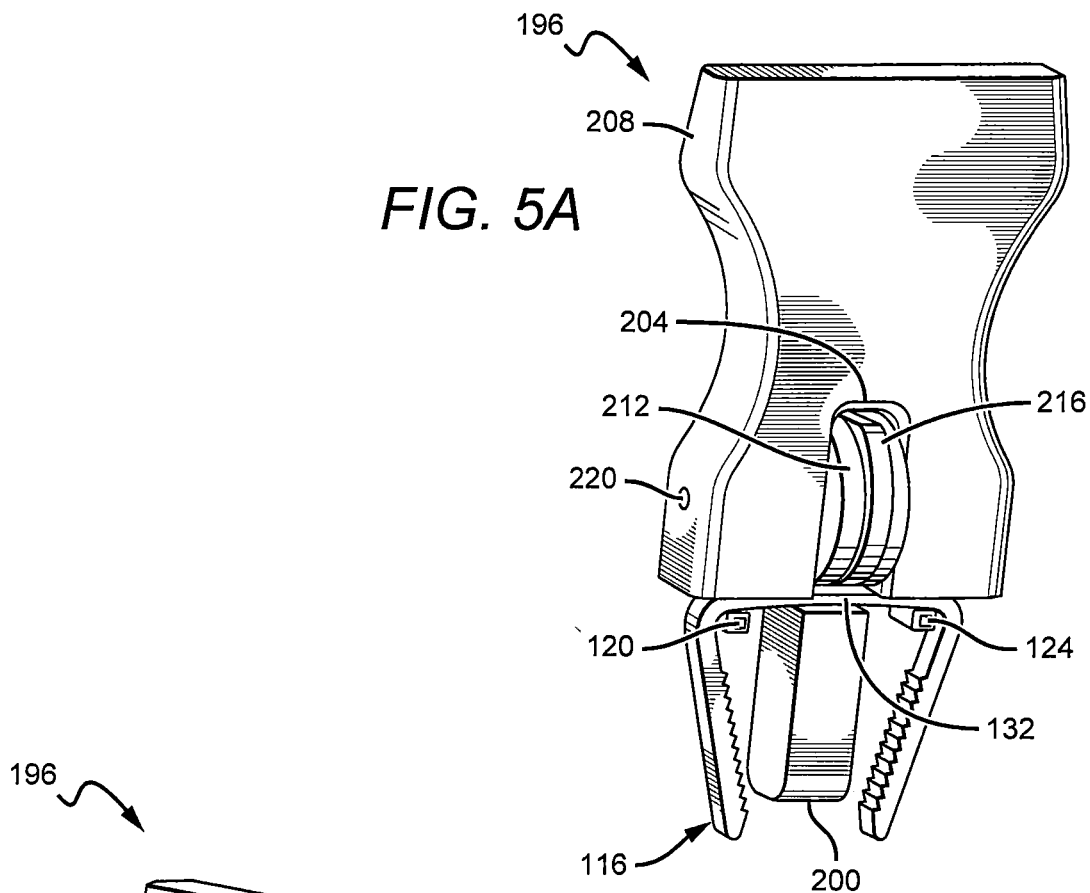
FIG. 5A illustrates an upper perspective view of an exemplary embodiment of a surgical bending instrument retaining a surgical staple in an initial configuration in accordance with the present disclosure.
Figure 5B:
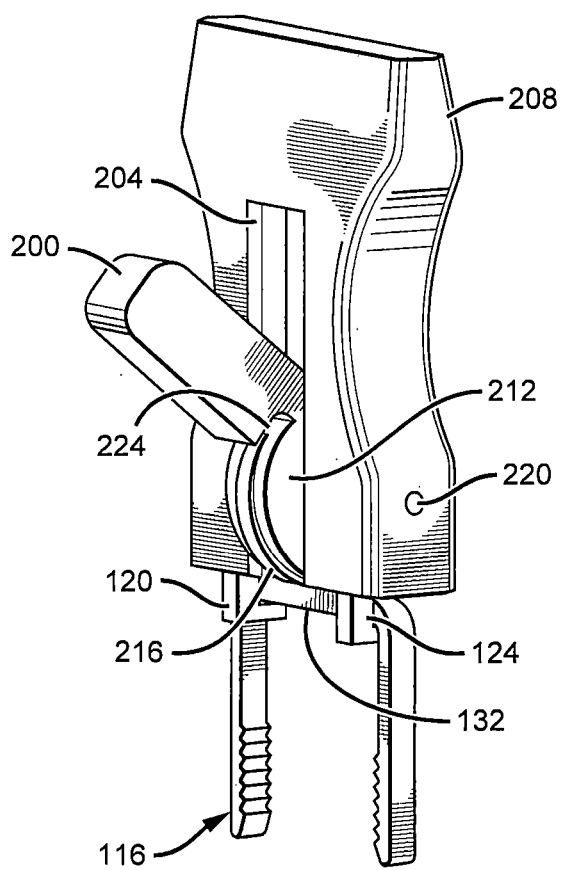
FIG. 5B illustrates an upper perspective view of the exemplary embodiment of the surgical bending instrument illustrated in FIG. 5A distracting the surgical staple in accordance with the present disclosure.

FIGS. 5A and 5B illustrate proximal views of an exemplary embodiment of a surgical bending instrument 196 retaining the surgical staple 116 in accordance with the present disclosure. The surgical bending instrument 196 illustrated in FIGS. 5A and 5B is similar to the surgical bending instrument 160 illustrated in FIGS. 4A-4B, with the exception that the instrument 196 comprises a center lever 200 rotatably positioned within an opening 204 of a body 208. As best illustrated in FIG. 5A, the center lever 200 comprises a wheel 212 and a cam 216 positioned on a periphery of the wheel. The wheel 212 is rotatably mounted on a pivot 220 within the body 208. Unlike previously described embodiments, in the embodiment of FIGS. 5A-5B, the wheel 212 is in direct contact with the crown 132, in absence of a separately, coupled driver. In the embodiment illustrated in FIGS. 5A-5B, the cam 216 operates substantially similarly to the driver described herein. It will be appreciated that the cam 216 is positioned on the wheel so as to exert a distally-directed force on the crown 132 when the center lever 200 is moved from a distal position, illustrated in FIG. 5A, to a proximal position shown in FIG. 5B. As described herein, the distally-directed force on the crown 132 distracts the surgical staple 116 such that the staple may be implanted in the bone of the patient.

As best illustrated in FIG. 5B, the center lever 200 further comprises a slot 224 adjacent to the wheel 212. It will be appreciated that the slot 224 advantageously allows the center lever 200 to be placed into the distal position while the surgical staple 116 is clasped in the first and second grips 120, 124. In some embodiments, the slot 224 is configured to cooperate with the first and second grips 120, 124 so as to retain the surgical staple 116 in the surgical bending instrument while the staple is in the initial configuration, as shown in FIG. 5A.

It should be understood that although embodiments of the surgical bending instrument have been discussed in combination with the surgical staple 116, the surgical bending instruments 100, 160, 196 are not to be limited to distracting surgical staples. Rather, the surgical bending instruments 100, 160, 196 may be used in various capacities other than as described herein, such as by way of non-limiting example, bending a bone fusion plate so as to tailor the plate to a specific anatomy of a patient's bone being treated. Accordingly, it is envisioned that the surgical bending instruments 100, 160, 196 may be packaged into sterile surgery-specific kits comprising other surgical tools and components, such as by way of non-limiting example, drill guides, drill sizers, tamps, forceps, staple removal tools, drills, temporary pins, drill depth stops, fusion bone plates, bone plate fasteners, compression screws, and the like. Further, the surgical bending instruments 100, 160, 196 preferably comprise a rigid material suitable for bending surgical implants, such as surgical staples and bone fusion plates, as described herein. In some embodiments, the surgical bending instruments 100, 160, 196 comprise metal, plastic, or a combination of the two.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A method for a surgical bending instrument for bending surgical implants, comprising:
    configuring a distal force applicator to:
        retain and distract a surgical implant;
        configure a driver to:
            move distally when a proximal handle is twisted clockwise, such that a surgical staple can be clasped between the driver and the first grip and the second grip; and
            move proximally when the proximal handle is twisted counterclockwise, such that the driver retracts from the surgical staple;
    configuring a body to support the distal force applicator; and
    forming a proximal handle for operating the distal force applicator.

2. The method of claim 1, wherein configuring the distal force applicator includes configuring a first grip and configuring a second grip to retain the surgical implant.

3. The method of claim 2, wherein configuring the distal force applicator includes configuring a driver to exert a distally-directed force so as to bend the surgical implant.

4. The method of claim 1, wherein configuring the body includes longitudinally extending a threaded hole within the body.

5. The method of claim 4, wherein configuring the distal force applicator includes threadably engaging a shaft within the hole such that a distal extension of the shaft comprises a driver of the distal force applicator.

6. The method of claim 5, wherein engaging the shaft includes fixedly coupling a proximal handle to the end of the shaft such that mechanical forces applied at the proximal handle are applied to the driver.

7. The method of claim 6, wherein coupling the proximal handle includes coupling the proximal handle such that rotating the proximal handle relative to the body moves the driver longitudinally relative to the body.

8. The method of claim 6, wherein configuring the distal force applicator includes engaging the driver with a distal extension of the shaft.

9. The method of claim 1, wherein configuring the distal force applicator includes configuring a lever comprising a wheel and a peripheral cam.

10. The method of claim 9, wherein configuring the distal force applicator includes mounting the wheel on a pivot within the body such that moving the lever proximally causes the cam to forcibly push a driver comprising the distal force applicator in a distal direction.

11. The method of claim 10, wherein configuring the distal force applicator includes mounting the wheel such that a surgical staple can be retained between the driver and a first grip and a second grip comprising the distal forced applicator.

12. The method of claim 11, wherein mounting the wheel includes configuring the cam such that moving the lever proximally distracts the surgical staple and moving the lever distally relaxes the surgical staple.

13. The method of claim 1, wherein configuring the distal force applicator comprises configuring the distal force applicator to distract a surgical staple for fixation of osteotomies and joint arthrodesis of the hands and feet.

14. The method of claim 1, wherein configuring the distal force applicator comprises configuring the distal force applicator to bend a bone fusion plate for tailoring the bone fusion plate to a specific anatomy of a target bone.

15. The method of claim 1, wherein configuring the distal force applicator includes disposing a driver between a first grip and a second grip that are fixated to the body.

16. The method of claim 15, wherein configuring the distal force applicator includes configuring the driver to forcibly contact a crown of a surgical staple that is supported by the first grip and the second grip.

17. The method of claim 16, wherein disposing the driver includes separating the first grip and the second grip by a distance that is comparable with the length of the crown.

18. The method of claim 17, wherein configuring the distal force applicator includes configuring the first grip and configuring the second grip to have an adjustable separation distance.

* * * * *